(12) United States Patent
Sakashita et al.

(10) Patent No.: US 9,255,937 B2
(45) Date of Patent: Feb. 9, 2016

(54) AUTOMATIC ANALYZER

(75) Inventors: Yukinori Sakashita, Hitachinaka (JP); Katsuaki Takahashi, Hitachinaka (JP); Yoshihiro Yamashita, Hitachinaka (JP); Taku Sakazume, Hitachinaka (JP)

(73) Assignee: HITACHI HIGH TECHNOLOGIES CORPORATION, Tokyo (JP)

( * ) Notice: Subject to any disclaimer, the term of this patent is extended or adjusted under 35 U.S.C. 154(b) by 390 days.

(21) Appl. No.: 13/809,280

(22) PCT Filed: Jul. 20, 2011

(86) PCT No.: PCT/JP2011/066403
§ 371 (c)(1),
(2), (4) Date: Feb. 4, 2013

(87) PCT Pub. No.: WO2012/011481
PCT Pub. Date: Jan. 26, 2012

(65) Prior Publication Data
US 2013/0125671 A1    May 23, 2013

(30) Foreign Application Priority Data

Jul. 20, 2010 (JP) ................. 2010-162414

(51) Int. Cl.
*G01N 35/00* (2006.01)
*G01N 35/10* (2006.01)
*G01N 35/04* (2006.01)

(52) U.S. Cl.
CPC ............ *G01N 35/10* (2013.01); *G01N 35/1081* (2013.01); *G01N 35/1016* (2013.01); *G01N 2035/0443* (2013.01); *G01N 2035/0444* (2013.01); *G01N 2035/0453* (2013.01); *G01N 2035/1025* (2013.01)

(58) Field of Classification Search
CPC ............. G01N 35/10; G01N 35/1016; G01N 35/1025; G01N 35/1081; G01N 2035/0443; G01N 2035/0444; G01N 2035/0453
See application file for complete search history.

(56) References Cited

U.S. PATENT DOCUMENTS 8,496,877 B2 * 7/2013 Yamazaki et al. .............. 422/67
2008/0257073 A1    10/2008 Tajima et al.

FOREIGN PATENT DOCUMENTS

| EP | 0290018 A2 | 11/1988 |
|---|---|---|
| EP | 1225450 A1 | 7/2002 |
| JP | 04-318451 A | 11/1992 |
| JP | 06-10868 U | 2/1994 |
| JP | 2000-206008 A | 7/2000 |
| JP | 2008-058127 A | 3/2008 |
| WO | 2006/062236 A1 | 6/2006 |

OTHER PUBLICATIONS

International Preliminary Report on Patentability received in International Application No. PCT/JP2011/066403 dated Feb. 21, 2013.

* cited by examiner

*Primary Examiner* — Daniel S Larkin
(74) *Attorney, Agent, or Firm* — Mattingly & Malur, PC

(57) ABSTRACT

Provided is an automatic analyzer that includes a suction nozzle, a detection container, and a detector. The suction nozzle suctions a sample and a solution used for the detection of the sample. The suctioned sample and the solution are supplied to the detection container. The detector detects a signal from the sample. In addition, a vessel for the sample and a container for the solution are disposed below the detection container.

10 Claims, 13 Drawing Sheets

AUTOMATIC ANALYZER

TECHNICAL FIELD

The present invention relates to an automatic analyzer, and more particularly to an automatic analyzer that uses a detector to detect a suction nozzle, which suctions a sample, and detects the sample suctioned by the suction nozzle.

BACKGROUND ART

Various automatic analyzers that are particularly used, for instance, in the fields of medicine and biotechnology include a detection system flow path mechanism in which a nozzle for suctioning a liquid is connected by way of a flow path and of a detector to a suction drive source for suctioning the liquid from the nozzle. Such automatic analyzers handle, for example, blood, serum, or urine as a sample and detect a specific biogenic substance, chemical substance, or other substance included in the sample.

As regards such automatic analyzers, efforts are being made to increase the accuracy of analysis in order to conduct highly reliable examinations with a high degree of precision. A method described, for instance, in Patent Document 1 is applicable to an analyzer that includes a suction nozzle for suctioning a liquid, a flow path connected to the suction nozzle, a suction drive source connected to the flow path to permit the suction nozzle to suction the liquid, a liquid container into which the suction nozzle is inserted to let the suction nozzle suction the liquid, and a transfer mechanism for transferring the liquid container to insert the suction nozzle into the liquid container. This analyzer suctions the liquid while retaining the relative positional relationship between the suction nozzle, the flow path, and a detector connected to the flow path.

PRIOR ART LITERATURE

Patent Document

Patent Document 1: JP-2008-58127-A

SUMMARY OF THE INVENTION

Problem to be Solved by the Invention

The method described in Patent Document 1 attempts to eliminate the cause of analysis failure due to a deformed flow path between the suction nozzle and the detector. Meanwhile, an automatic analyzer that successively executes an analysis cycle is requested to use a plurality of liquids and a plurality of liquid containers during each execution of the analysis cycle and shorten the time required for the execution of the analysis cycle. Hence, it is necessary to efficiently move the liquid containers and supply the liquids to the liquid containers for the purpose of causing the suction nozzle to suction each liquid in accordance with the analysis cycle.

However, no solution is disclosed in Patent Document 1 for a problem about an analysis cycle efficiency decrease due to limitations on the movements of the liquid containers and on the timing of liquid supply or for a problem about analysis accuracy decrease due to improper control of the amounts of liquids to be supplied to the liquid containers. Further, no optimum flow path shape is disclosed in Patent Document 1. The cause of analysis failure due to a deformed flow path is successfully eliminated. However, as the flow path between the suction nozzle and the detector is long, it is necessary to provide the flow path with some bends and joints. This may decrease the performance of analysis.

In view of the above problems with a prior art, the present invention has been made to provide an automatic analyzer capable of shortening an analysis cycle and making analyses with high accuracy.

Means for Solving the Problem

The present invention provides an automatic analyzer that includes a suction nozzle, a detection container, and a detector. The suction nozzle suctions a sample and a solution used for the detection of the sample. The suctioned sample and the solution are supplied to the detection container. The detector detects a signal from the sample. A vessel for the sample and a container for the solution are disposed below the detection container.

The present invention also provides an automatic analyzer that includes a suction nozzle and a container. The suction nozzle suctions a solution that is used to detect a sample. The container retains the solution that is used to detect the sample. The automatic analyzer further includes a drive mechanism, which drives a container retaining member to bring a vessel for the sample and the container for the solution close to the suction nozzle, and a nozzle, which supplies the solution to the vessel and the container. The nozzle moves in accordance with the movement of the vessel or the container moved by the drive mechanism.

Effects of the Invention

The present invention makes it possible to provide an automatic analyzer capable of supplying a liquid with high efficiency, shortening an analysis cycle, and making analyses with high accuracy.

MODE FOR CARRYING OUT THE INVENTION

An embodiment of the present invention will now be described with reference to FIGS. 1 to 15.

Overall Configuration of Automatic Analyzer

Figure 1:
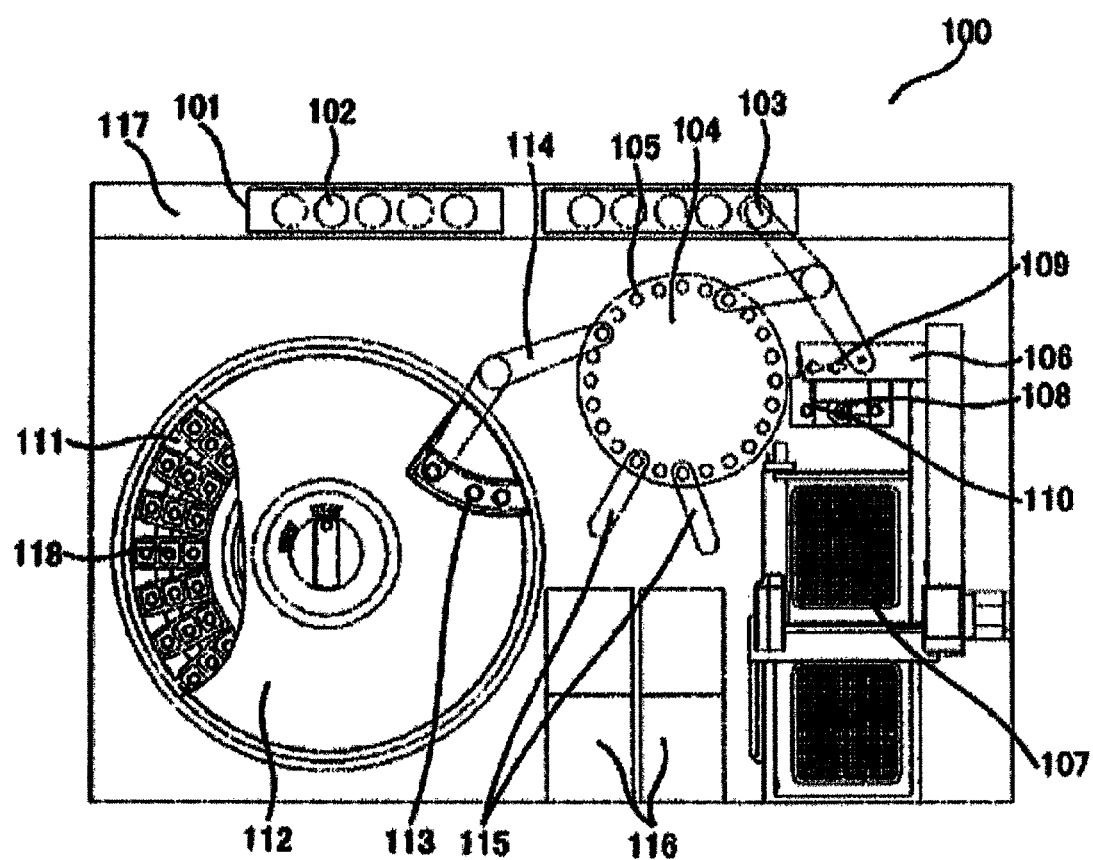
FIG. 1 is a diagram illustrating the overall configuration of an analyzer.

First of all, the overall configuration of an automatic analyzer according to an embodiment of the present invention will be described with reference to FIG. 1. A sample container 102 for retaining a sample is mounted on a rack 101 of the automatic analyzer 100. A rack transport line 117 is used to transport the rack 101 to a sample dispensing position near a sample dispensing nozzle 103.

A plurality of reaction vessels 105 can be mounted on an incubator disk 104. The incubator disk 104 provides rotational transfer so that the circumferentially disposed reaction vessels 105 can be respectively transferred to predetermined positions.

A sample dispensing tip/reaction vessel transport mechanism 106 can move in three directions (in the X-, Y-, and Z-axis directions). The sample dispensing tip/reaction vessel transport mechanism 106 transports sample dispensing tips and reaction vessels by moving within a range defined by predetermined locations of a sample dispensing tip/reaction vessel retaining member 107, a reaction vessel agitation mechanism 108, a sample dispensing tip/reaction vessel disposal hole 109, a sample dispensing tip mounting position 110, and the incubator disk 104.

A plurality of unused reaction vessels 105 and a plurality of sample dispensing tips can be set in the sample dispensing tip/reaction vessel retaining member 107. The sample dispensing tip/reaction vessel transport mechanism 106 moves to a location above the sample dispensing tip/reaction vessel retaining member 107, descends to grasp an unused reaction vessel, ascends, moves to a location above a predetermined position of the incubator disk 104, and descends to set the reaction vessel 105.

Next, the sample dispensing tip/reaction vessel transport mechanism 106 moves to a location above the sample dispensing tip/reaction vessel retaining member 107, descends to grasp an unused sample dispensing tip, ascends, moves to a location above the sample dispensing tip mounting position 110, and descends to set the sample dispensing tip.

The sample dispensing nozzle 103 can pivot and move up and down. Hence, the sample dispensing nozzle 103 pivots to a location above the sample dispensing tip mounting position 110, descends, and sets the sample dispensing tip by press-fitting it into a leading end of the sample dispensing nozzle 103. The sample dispensing nozzle 103 to which the sample dispensing tip is attached moves to a location above the sample container 102 mounted on the rack 101, descends, and suctions a predetermined amount of sample retained by the sample container 102. After suctioning the sample, the sample dispensing nozzle 103 moves to a location above the incubator disk 104, descends, and discharges the sample to an unused reaction vessel 105 retained by the incubator disk 104. After the sample is discharged, the sample dispensing nozzle 103 moves to a location above the sample dispensing tip/reaction vessel disposal hole 109 and discards the used sample dispensing tip from the sample dispensing tip/reaction vessel disposal hole 109.

A plurality of reagent cassettes 118 are placed on a reagent compartment 111. A reagent compartment cover 112 is installed over the reagent compartment 111 so that the interior of the reagent compartment 111 is maintained at a predetermined temperature. A part of the reagent compartment cover 112 is provided with a reagent compartment cover opening 113. A reagent dispensing nozzle 114 can rotate and move up and down. Hence, the reagent dispensing nozzle 114 rotates to a location above the reagent compartment cover opening 113, descends, inserts a leading end of the reagent dispensing nozzle 114 into a reagent within a predetermined reagent container, and suctions a predetermined amount of reagent. Next, the reagent dispensing nozzle 114 ascends, rotates to a location above a predetermined position of the incubator disk 104, and discharges the reagent to the reaction vessel 105.

The incubator disk 104 rotates so that the reaction vessel 105 to which the sample and the reagent have been discharged moves to a predetermined position. The sample dispensing tip/reaction vessel transport mechanism 106 then transports the reaction vessel 105 to the reaction vessel agitation mechanism 108. The reaction vessel agitation mechanism 108 imparts rotary motion to the reaction vessel to agitate and mix the sample and reagent in the reaction vessel. After completion of agitation, the sample dispensing tip/reaction vessel transport mechanism 106 returns the reaction vessel to a predetermined position of the incubator disk 104.

A reaction vessel transport mechanism 115 can rotate and move up and down. When the reaction vessel 105 has been placed on the incubator disk 104 for a predetermined period of reaction time after the sample and reagent are dispensed and agitated, the reaction vessel transport mechanism 115 moves to a location above the reaction vessel 105, descends, grasp the reaction vessel 105, and transports the reaction vessel 105 to a detection unit 116 by rotational transfer.

The drive and drive timing of the above components are controlled by a control device (e.g., computer) not shown.

Detection Process

A detection process according to the present invention will now be described in detail.

Figure 15:
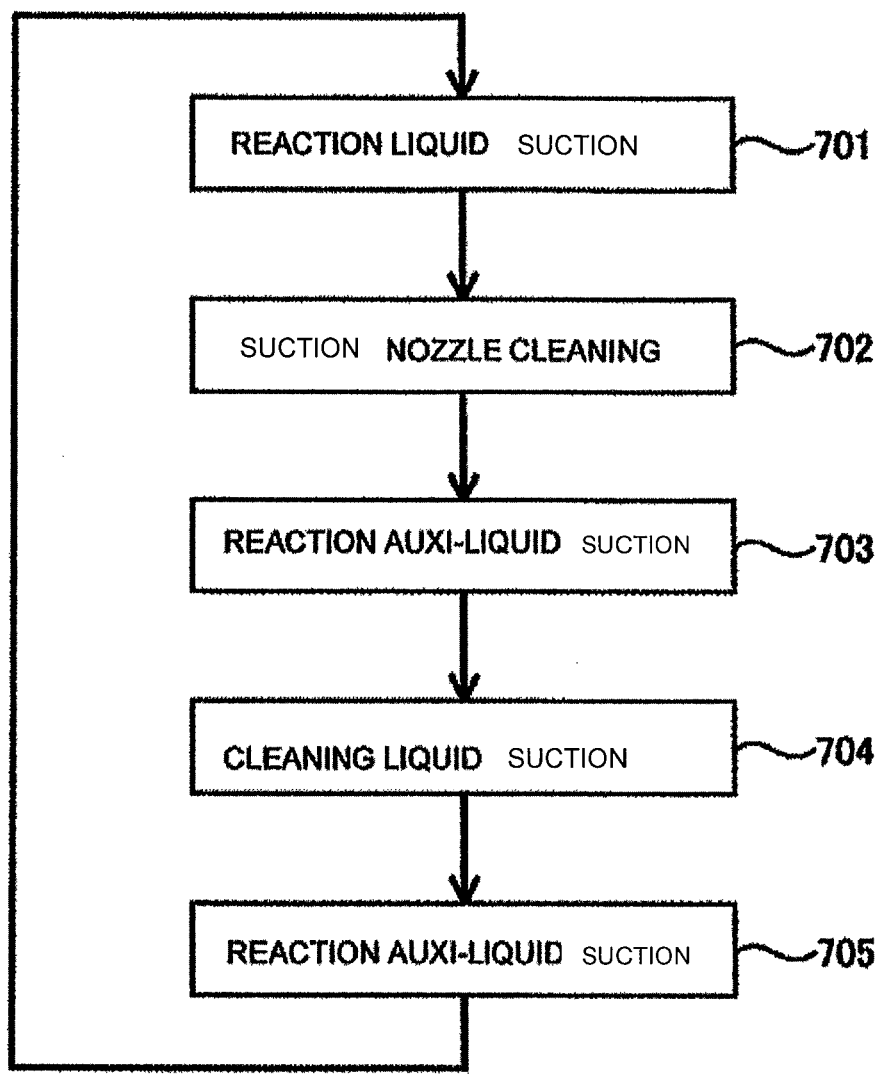
FIG. 15 is a flowchart illustrating an analysis cycle.

As indicated in FIG. 15, the following steps are performed to analyze a sample in the detection unit 116. The steps will be described with reference to FIGS. 2 and 15.

The following description is given on the assumption that the automatic analyzer handles magnetic particles.

Step 1 Suctioning of Reaction Liquid 701

Having been placed on the incubator disk 104 for the predetermined period of reaction time, the reaction vessel 105 is transported to the detection unit 116. A reaction solution in the reaction vessel 105 is suctioned by a suction nozzle 205 shown in FIG. 2 and introduced into a detection container 202. A magnetic particle complex contained in the reaction solution is magnetically captured by the inside of the detection container 202.

Step 2 Cleaning of Suction Nozzle 702

The suction nozzle 205 that has suctioned the reaction solution is cleaned. In the next step, the suction nozzle 205 suctions a reaction auxiliary liquid. The suction nozzle 205 is cleaned to prevent the reaction solution attached to the suction nozzle 205 from remaining in the step of reaction auxiliary liquid and in the subsequent steps.

Step 3 Suctioning of Reaction Auxiliary Liquid 703

An unnecessary portion of the reaction solution introduced into the detection container 202 in step 1 is removed except for the magnetically captured magnetic particle complex and substituted by the reaction auxiliary liquid. For such substitution, the suction nozzle 205 suctions the reaction auxiliary liquid and introduces it into the detection container 202.

After the reaction auxiliary liquid is introduced into the detection container 202, a detection marker for the magnetic particle complex is detected to determine the quantity of a measurement target (biogenic substance or chemical substance in the sample).

Step 4 Suctioning of Cleaning Liquid 704

After the detection marker is detected, the suction nozzle 205 suctions a cleaning liquid in order to clean magnetic particles and reaction auxiliary liquid that remain in the detection container 202.

Step 5 Suctioning of Reaction Auxiliary Liquid 705

As a preparation for the next detection, the cleaning liquid remaining in the detection container 202 in step 4 is removed and substituted by the reaction auxiliary liquid. For such substitution, the suction nozzle 205 suctions the reaction auxiliary liquid and introduces it into the detection container 202.

After completion of step 5, steps 1 to 5 are repeated to make a plurality of analyses.

Configuration of Present Invention

The configuration of the present invention will now be described.

The present invention provides a mechanism that makes analyses with high efficiency by efficiently suctioning the reaction solution, cleaning liquid, and reaction auxiliary liquid used for analyses and cleaning the suction nozzle 205.

The mechanism will be described below with reference to FIGS. 3, 4, 5, 6, and 7.

Figure 3:
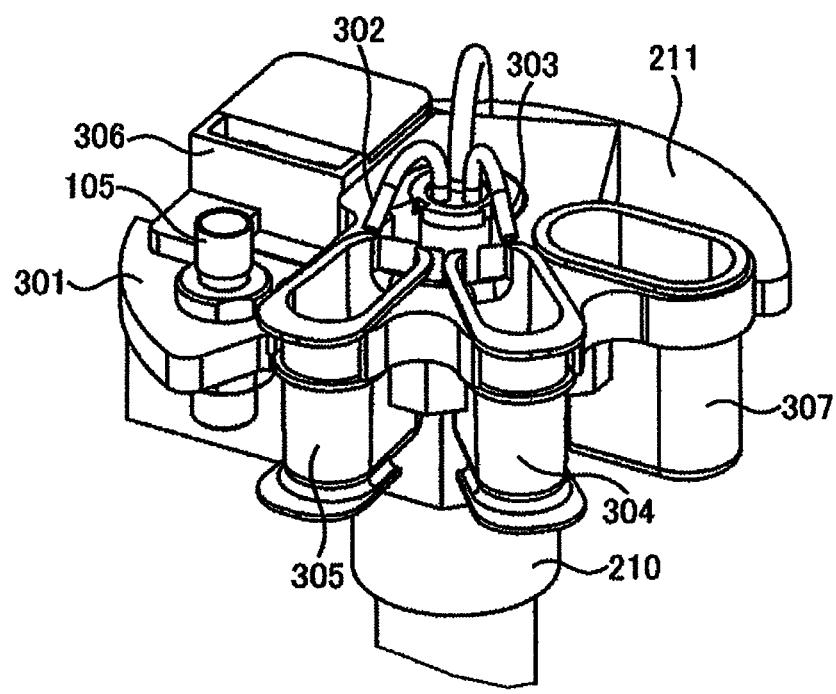
FIG. 3 is a perspective view of a container retaining member transfer mechanism.
Figure 4:
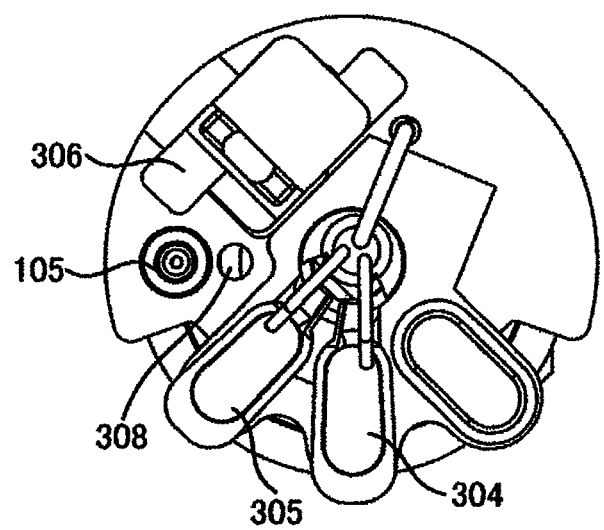
FIG. 4 is a top view of the container retaining member transfer mechanism.
Figure 5:
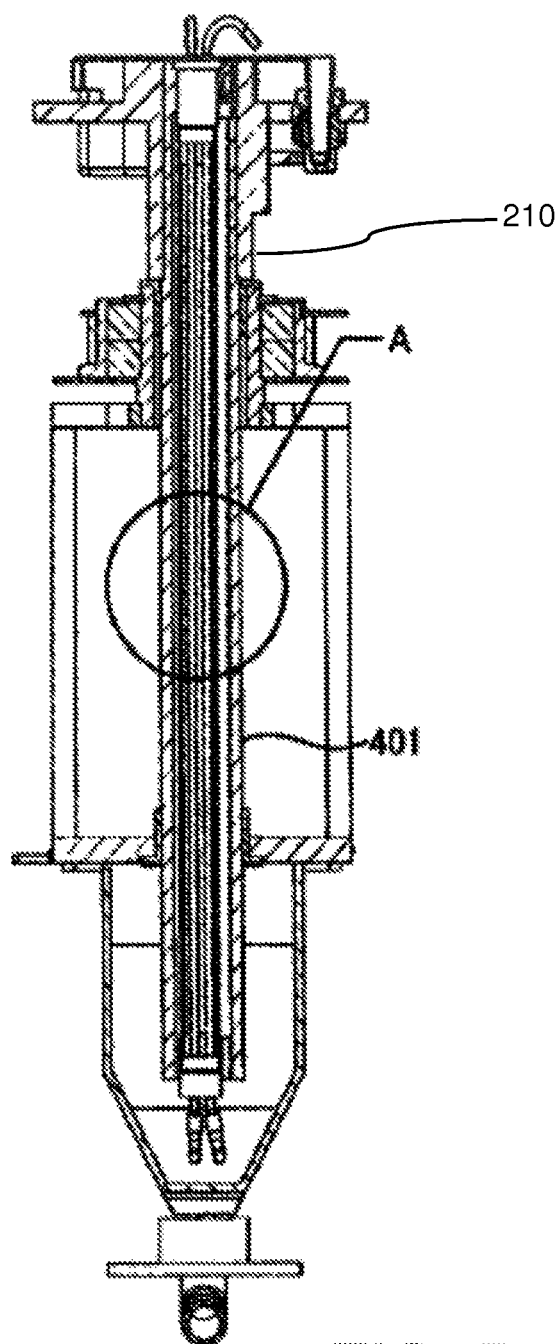
FIG. 5 is a cross-sectional view illustrating the interior of a hollow rotating shaft in the container retaining member transfer mechanism.

FIG. 3 is a perspective view of a container retaining member transfer mechanism according to the present invention. FIG. 4 is a top view thereof.

A container retaining member 211 has a reaction vessel mounting place 301 at which the reaction vessel 105 that has been placed on the incubator disk 104 for the predetermined period of reaction time is mounted. A cleaning tank 306 for cleaning the suction nozzle 205, a cleaning liquid container 305 for retaining the cleaning liquid, and a reaction auxiliary liquid container 304 for retaining the reaction auxiliary liquid are mounted on the container retaining member 211. In the present embodiment, a special cleaning liquid container 307 is additionally mounted on the container retaining member 211. The special cleaning liquid container 307 retains a special cleaning liquid for the maintenance of the automatic analyzer.

The container retaining member transfer mechanism 210 rotates and vertically drives the container retaining member 211. In the automatic analyzer 100 according to the present invention, a fixed, straight pipe is connected between the suction nozzle 205 and the detection container 202 in order to eliminate the cause of analysis failure due to a deformed flow path. Meanwhile, as the suction nozzle 205 cannot move, the container retaining member 211 is driven by the container retaining member transfer mechanism 210 so as to move the reaction vessel 105, the cleaning tank 306, the cleaning liquid container 305, and the reaction auxiliary liquid container 304 toward the suction nozzle 205.

The container retaining member 211 may be configured so that individual containers are disposed around a rotation axis or disposed in a row. In this instance, the container retaining member transfer mechanism 210 drives the container retaining member 211 linearly and vertically. When the container retaining member 211 is configured so that the individual containers are disposed around the rotation axis, the amount of movement provided by the container retaining member transfer mechanism 210 can be decreased to avoid the spill and bubbling of the liquids in the containers during transfer.

As the container retaining member transfer mechanism 210 transfers the containers by moving the container retaining member 211, the containers can be steadily transferred with a simple drive mechanism as compared to a case where the containers are individually transferred. The container retaining member 211 and the container retaining member transfer mechanism 210 may be integrally formed.

A cleaning liquid supply nozzle 302 and a reaction auxiliary liquid supply nozzle 303 are also provided. The cleaning liquid supply nozzle 302 replenishes the cleaning liquid container 305 with the cleaning liquid. The reaction auxiliary liquid supply nozzle 303 replenishes the reaction auxiliary liquid container 304 with the reaction auxiliary liquid. The cleaning liquid supply nozzle 302 and the reaction auxiliary liquid supply nozzle 303 move together with the cleaning liquid container 305 and the reaction auxiliary liquid container 304 with the leading ends of the cleaning liquid supply nozzle 302 and reaction auxiliary liquid supply nozzle 303 respectively oriented toward the cleaning liquid container 305 and reaction auxiliary liquid container 304. This is accomplished when the cleaning liquid supply nozzle 302 and the reaction auxiliary liquid supply nozzle 303 are fastened to the container retaining member 211 or to the container retaining member transfer mechanism 210.

Figure 6:
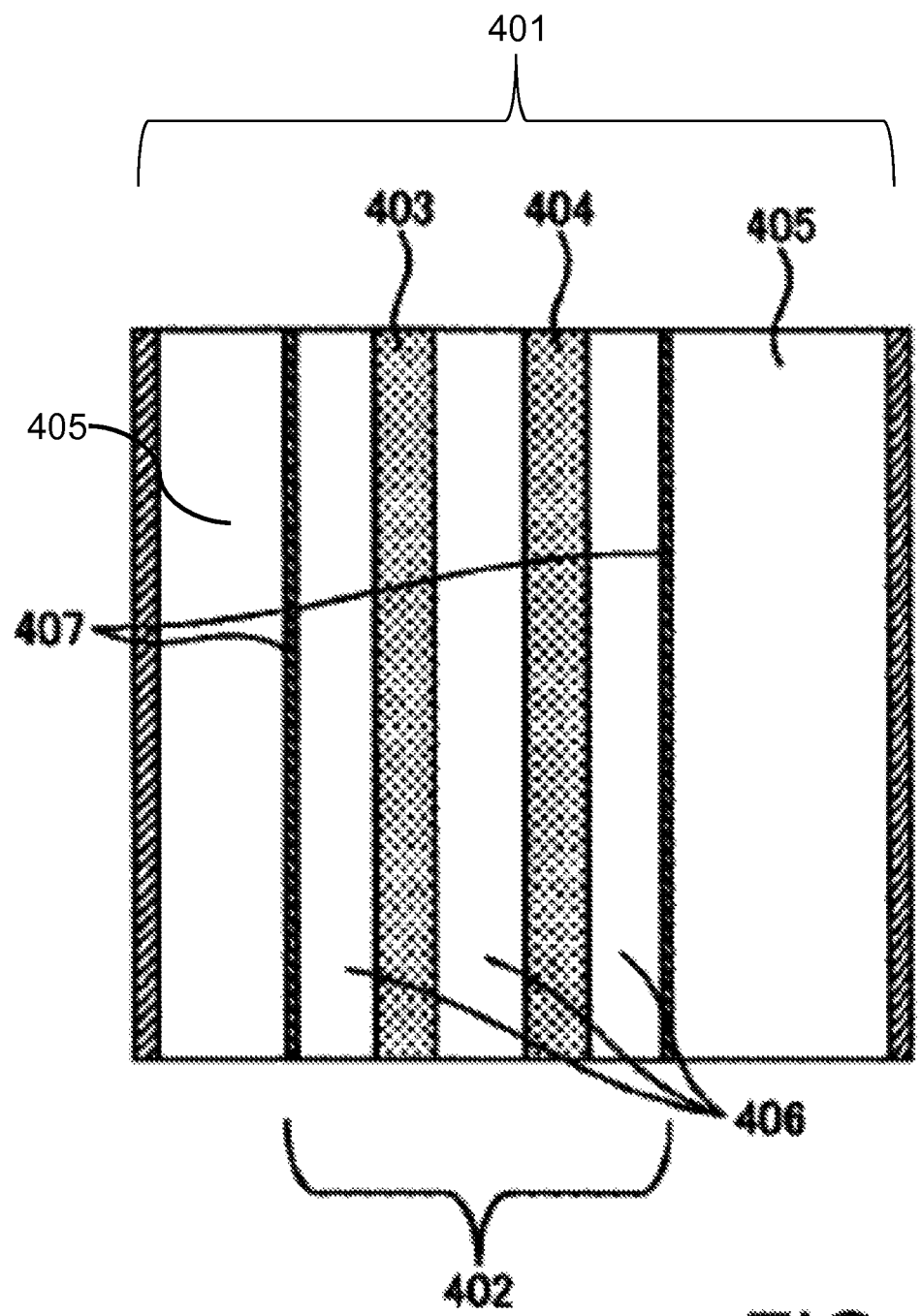
FIG. 6 is a detailed, cross-sectional view illustrating the interior of the hollow rotating shaft in the container retaining member transfer mechanism.
Figure 7:
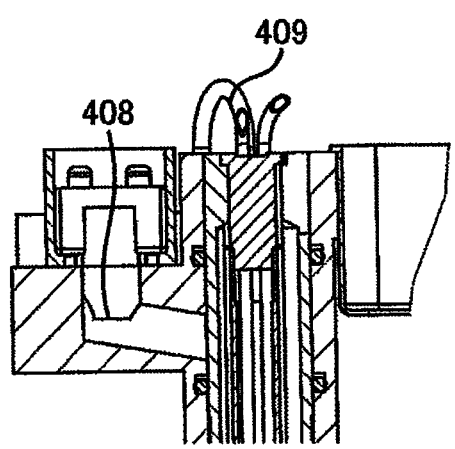
FIG. 7 is a cross-sectional view of a suction nozzle cleaning tank in the container retaining member transfer mechanism.

The flow path configuration of a hollow internal piping included in the container retaining member transfer mechanism 210 and a temperature retention mechanism 401 included therein will now be described with reference to FIGS. 5, 6, 7, and 9. FIG. 6 is a detail view of area A of FIG. 5.

As indicated by the detailed view of area A (FIG. 6), which shows a cross-section of the container retaining member transfer mechanism 210, the interior of the temperature retention mechanism 401 is formed by a hollow internal piping 402 and a drain piping 405. The hollow internal piping 402 includes a reaction auxiliary liquid piping 403 and a cleaning liquid piping 404, which are respectively connected to the reaction auxiliary liquid supply nozzle 303 and to the cleaning liquid supply nozzle 302. The reaction auxiliary liquid and the cleaning liquid, which are maintained at a predetermined temperature by a temperature control mechanism 602 (shown in FIG. 9) disposed external to the container retaining member transfer mechanism 210, respectively flow into the reaction auxiliary liquid piping 403 and into the cleaning liquid piping 404.

The cleaning liquid (cleaning water in the present embodiment) for the suction nozzle 205 flows in a hollow portion 406 of the hollow internal piping 402. The cleaning water is also maintained at a predetermined temperature by the temperature control mechanism 602 disposed external to the container retaining member transfer mechanism 210. The cleaning water additionally functions to provide increased heat retention for the reaction auxiliary liquid and cleaning liquid. The cleaning water flows into the cleaning tank 306 through a piping 409, cleans the suction nozzle 205 in the cleaning tank 306, and then flows into the drain piping 405 through a cleaning tank drain 408. Although the drain piping is positioned adjacent to the hollow internal piping, a thermal insulator 407 is disposed between the drain piping and the hollow internal piping. Therefore, the flow of heat from the drain piping is blocked to keep the temperature in the hollow internal piping 402 unchanged.

A temperature control mechanism for an area in which the container retaining member transfer mechanism 210 is located will now be described. The container retaining member transfer mechanism 210 is disposed in a semi-closed space that is separated by a cover 601 installed over lateral and lower surfaces of the detection unit 116. In the semi-closed space, air is controlled by a circulating air temperature control mechanism 605 and discharged from a circulating air outlet 606 so that the area in which the container retaining member transfer mechanism 210 is located is maintained at a predetermined temperature.

Detailed Description of Detection Unit

Figure 8:
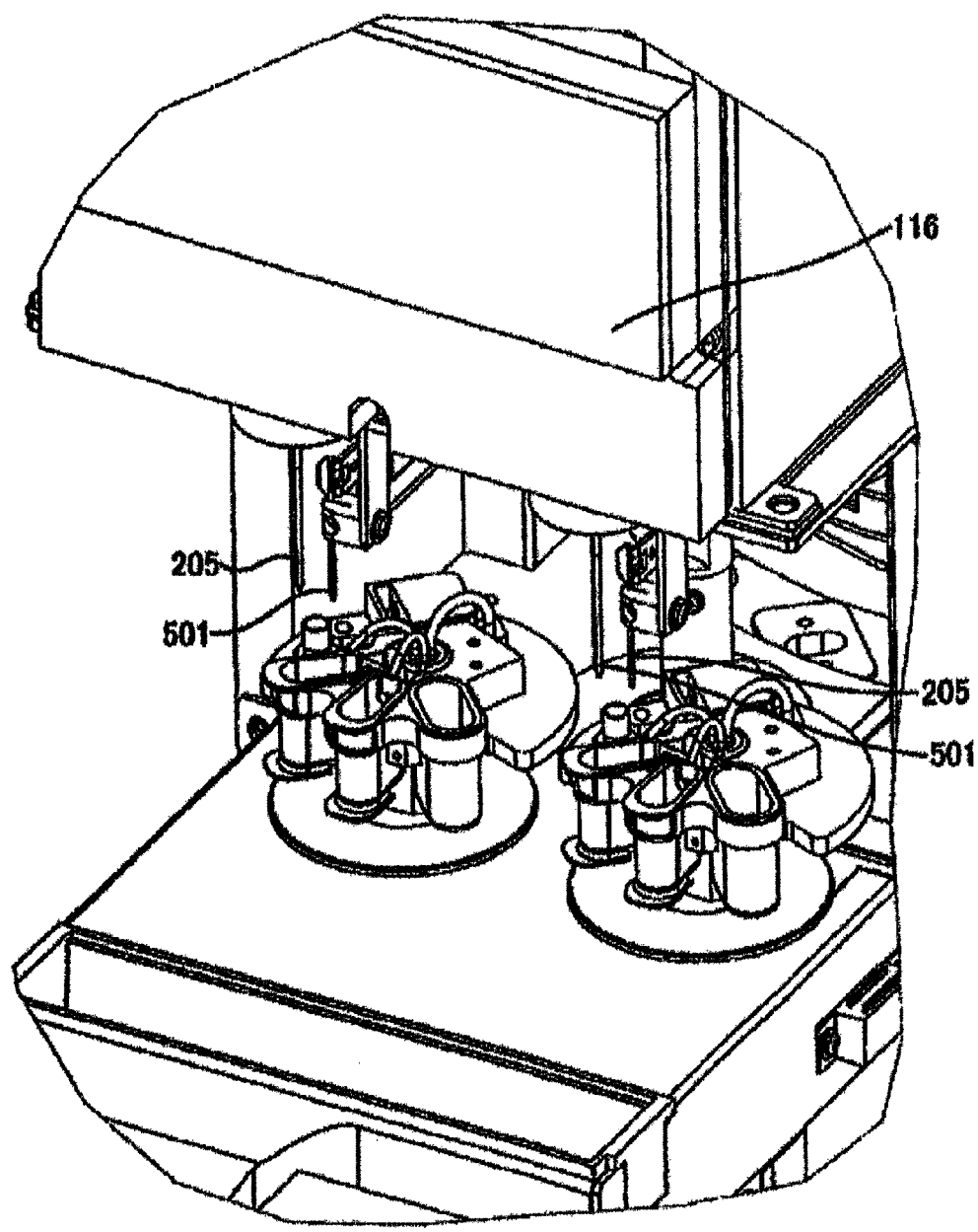
FIG. 8 is a perspective view illustrating a detection unit and the container retaining member transfer mechanism.
Figure 9:
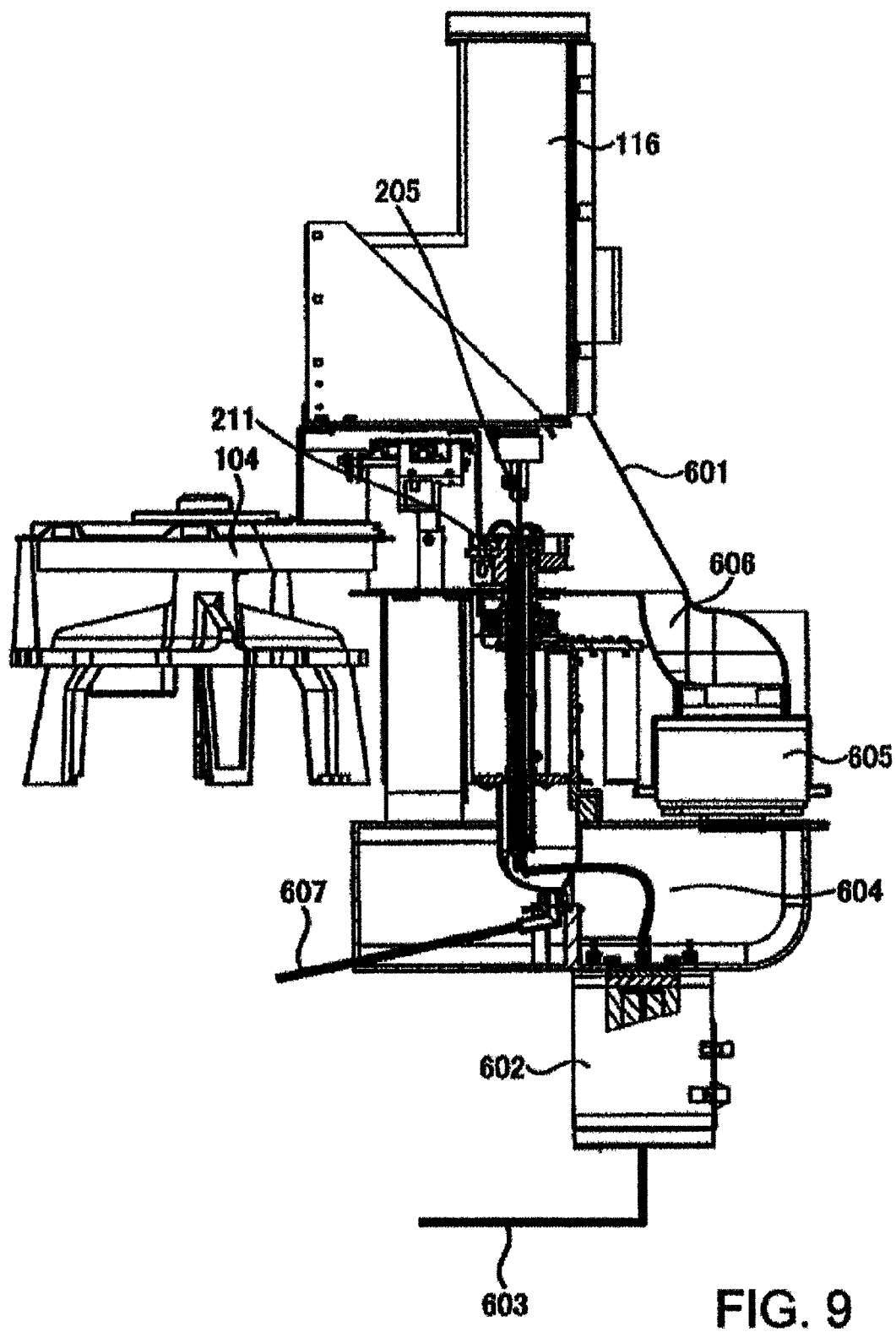
FIG. 9 is a cross-sectional view illustrating the detection unit, container retaining member transfer mechanism, and other components.

FIG. 8 is a perspective view illustrating the detection unit and the container retaining member transfer mechanism.

The detection unit 116 is connected to a liquid level detection probe 501 that detects a liquid level. The liquid level detection probe 501 is disposed so that its leading end is flush with the suction nozzle 205. Further, the liquid level detection probe 501 is electrically connected to the suction nozzle 205. Liquid level detection is achieved on the basis of electrical conduction that occurs when both the suction nozzle 205 and the liquid level detection probe 501 come into contact with an electrically conductive liquid.

In the present embodiment, two units of the detection unit 116 and two units of the reaction vessel transport mechanism 115 are employed so that a parallel analysis can be made by two detection mechanisms to double the efficiency of an analysis process.

Figure 2:
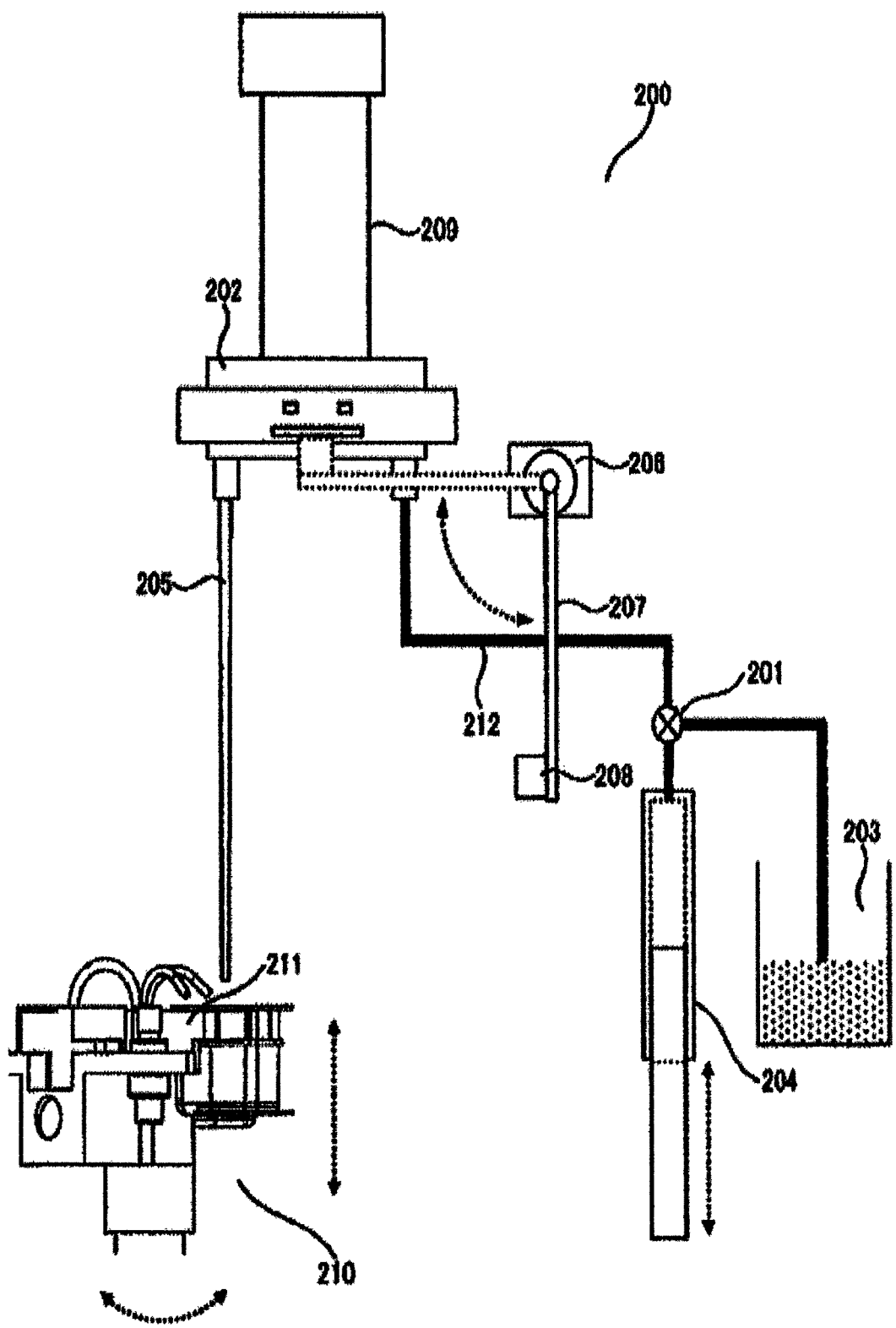
FIG. 2 is a diagram illustrating the configuration of a detection mechanism.

In the detection unit 116, the suction nozzle 205 is directly connected to the inlet of the detection container 202 as shown in FIG. 2, and the individual containers on the container retaining member 210 are disposed directly below (vertically below) the inlet of the detection container 202. This provides the following two advantages. Firstly, the distance between each container and the detection container 202 is shortened to substantially reduce the time required for each liquid to pass through the suction nozzle. This contributes to the shortening of an analysis cycle. Secondly, the distance that each liquid travels is shortened to inhibit each liquid from adhering to an inner wall. This contributes to the improvement of analysis performance. Further, as the suction nozzle 205 is shaped like a straight pipe, the velocity distribution of a liquid in the flow path readily becomes uniform. This helps inhibit solution components from adhering to the inner wall of the flow path. Particularly, if the solution is more or less stagnant in a situation where a magnetic particle complex is used, the magnetic particle complex accumulates. It is therefore preferred that the flow path of a liquid be linearly shaped to provide a uniform liquid flow. A flow path made of a straight pipe may be disposed between the suction nozzle 205 and the detection container 202.

To achieve the above-described object, the individual containers are disposed directly below (vertically below) the inlet of the detection container 202. In addition, the suction nozzle 205 is directly connected to the inlet of the detection container 202 or a flow path made of a straight pipe is disposed between the suction nozzle 205 and the detection container 202.

The relationship between the individual steps of the detection process and the configuration according to the present invention will now be described in detail.

Step 1

Figure 10:
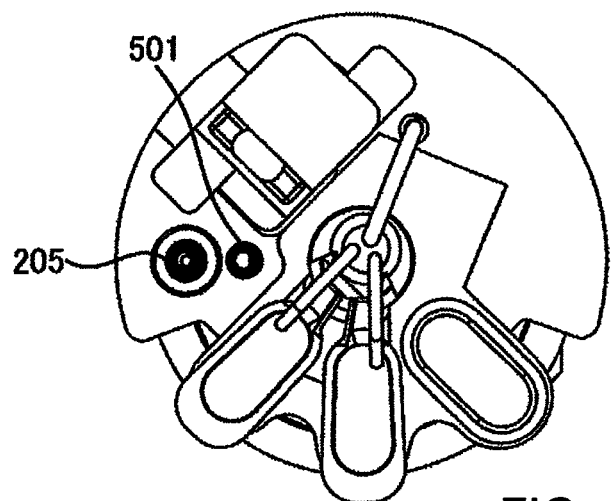
FIG. 10 is a plan view of the container retaining member transfer mechanism (reaction liquid suction position).

The reaction vessel transport mechanism 115 in a detection section transports the reaction vessel 105 from the incubator disk 104 to the detection unit 116. The reaction vessel 105 is then set at the reaction vessel mounting place 301 of the container retaining member 211 of the container retaining member transfer mechanism 210 located below the detection unit 116. Next, the container retaining member 211 rotates so that the reaction vessel 105 moves to a location directly below the suction nozzle 205 protruded from the detection unit 116, as shown in FIG. 10. The container retaining member 211 then moves upward to insert the suction nozzle 205 into a reaction liquid in the reaction vessel.

In the above instance, the liquid level detection probe 501 positioned adjacent to the suction nozzle 205 is not inserted into the reaction vessel 105, but is inserted into a liquid level detection probe hole 308 in a liquid retaining member provided to avoid interference with the liquid retaining member.

The suction nozzle 205 is inserted until it bottoms in the reaction vessel. However, the reaction vessel mounting place 301 is structured to be elastically movable downward relative to the container retaining member so that the suction nozzle 205 is pressed against the bottom of the reaction vessel at a predetermined pressure.

While the suction nozzle 205 is inserted into the reaction vessel, the detection container 202 side of a flow path changeover valve 201 disposed in a flow path 212 routed through the suction nozzle 205 and a liquid supply syringe 204 is opened with a drain 203 side closed. While this state is maintained, the liquid supply syringe 204 is driven in the direction of solution suctioning to introduce the reaction solution into the detection container 202 through the flow path 212. In this instance, a magnet drive motor 206 rotationally drives a magnet arm 207 through 90 degrees so that a magnetic particle capture magnet 208 attached to the leading end of the magnet arm 207 is positioned close to a location directly below the detection container 202. Consequently, the magnetic particle complex, which includes an analysis target and detection marker and is contained in the reaction solution passing through the detection container 202, is magnetically captured by the inside of the detection container 202.

Step 2

Figure 11:
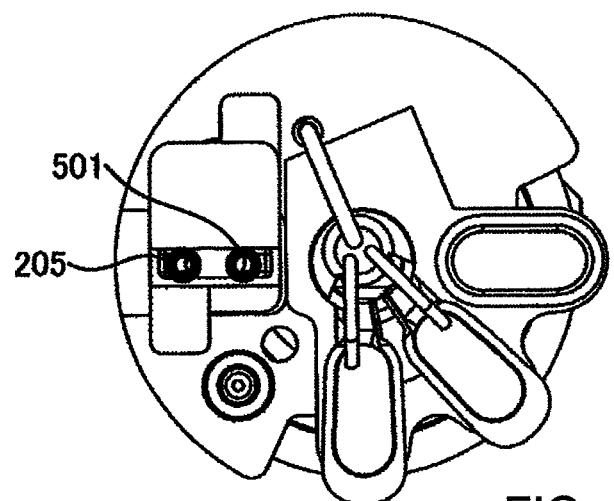
FIG. 11 is a plan view of the container retaining member transfer mechanism (suction nozzle cleaning position).

After the reaction solution is suctioned by the suction nozzle 205, the container retaining member 211 moves downward to extract the suction nozzle 205 from the solution in the reaction vessel 105. The container retaining member 211 then rotates to move the cleaning tank 306 to a location directly below the suction nozzle 205 as shown in FIG. 11. Next, the container retaining member 211 moves upward to insert the suction nozzle 205 and the liquid level detection probe 501 into the cleaning tank 306. The cleaning tank 306 has a cleaning liquid supply hole. Cleaning water supplied from the cleaning liquid supply hole is discharged toward the outer walls of the suction nozzle 205 and liquid level detection probe 501 to remove the reaction solution attached to the outer wall of the suction nozzle 205. The used cleaning water is then discharged into the drain 408 disposed at the bottom of the cleaning tank 306.

A flow path connected to the cleaning liquid supply hole is connected to the hollow portion 406 for suction nozzle cleaning water distribution, which is included in the hollow of a rotation shaft of the container retaining member transfer mechanism 210, and to a flow path 603 that communicates with a liquid supply source through the temperature control mechanism 602 disposed external to the container retaining member transfer mechanism 210. This flow path is disposed so as not to obstruct the rotation and vertical movement of the container retaining member 211. The temperature control mechanism 602 exercises control to maintain the supplied liquid at a predetermined temperature. A flow path connected to the drain 408 located at the bottom of the cleaning tank is connected to a drain flow path 607, which is disposed external to the container retaining member 211, through the drain piping 405 in the hollow of a rotation shaft of the container retaining member 211, and is disposed so as not to obstruct the rotation and vertical movement of the container retaining member 211. The cleaning of the suction nozzle 205 is performed in order to inhibit the risk of carrying the reaction solution over to the next step of the analysis cycle by way of the suction nozzle 205.

Step 3

Figure 12:
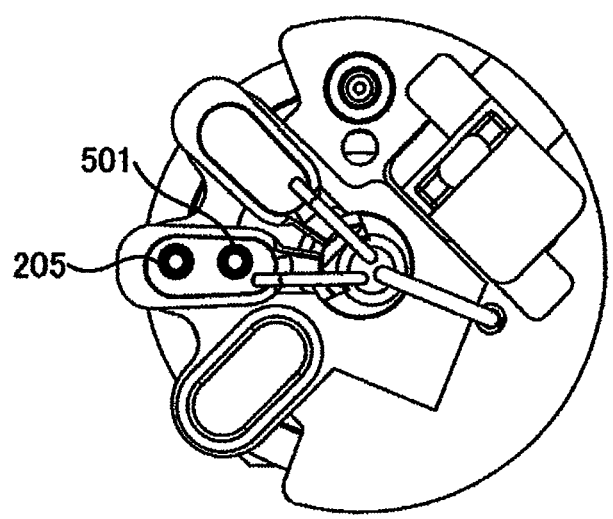
FIG. 12 is a plan view of the container retaining member transfer mechanism (reaction auxiliary liquid suction position).

After the suction nozzle 205 is cleaned, the container retaining member 211 moves downward to remove the suction nozzle 205 and the liquid level detection probe 501 from the cleaning tank 306. Next, the container retaining member 211 is rotationally transferred to move the reaction auxiliary liquid container 304 to a location directly below the suction nozzle 205 as shown in FIG. 12. The container retaining member 211 then moves downward to insert the suction nozzle 205 and the liquid level detection probe 501 into the reaction auxiliary liquid. In this instance, the liquid level detection probe 501 detects the level of the reaction auxiliary liquid, and the amount of upward movement of the container retaining member 211 is controlled so that the depth of insertion of the suction nozzle 205 into the reaction auxiliary liquid container 304 is maintained at a predetermined value. Positional arrangement is made so that the reaction vessel mounting place 301 can come close to the incubator disk 104 and to the reaction vessel transport mechanism 115 when the container retaining member 211 rotates and vertically moves in the above instance. After the container retaining member 211 rotates and vertically moves, the reaction vessel 105 at the reaction vessel mounting place 301 of the container retaining member 211 is captured by the reaction vessel transport mechanism 115 and transferred to a disposal reaction vessel mounting place on the incubator disk 104. As described above, when the positional arrangement of the containers on the container retaining member 211 is determined in such a manner that the reaction vessel transport mechanism 115 can access the reaction vessel mounting place 301 of the container retaining member 211 while the suction nozzle 205 is accessing the reaction auxiliary liquid container 304, the time required for analysis can be reduced.

The suction nozzle 205 inserted into the reaction auxiliary liquid suctions the reaction auxiliary liquid. While the magnetic particle complex is magnetically captured by the detection container 202, the reaction solution remaining in the detection container 202 is eliminated and substituted by the reaction auxiliary liquid. The reaction auxiliary liquid supply nozzle 303 is fixedly disposed on the container retaining member transfer mechanism 210 or on the container retaining member 211 so that the container retaining member 211 retains its relative positional relationship to the reaction auxiliary liquid container 304 even when the container retaining member 211 is rotating and vertically moving. Therefore, a steady, efficient liquid supply operation can be performed while limitations imposed by the operation of the container retaining member transfer mechanism 210 and by the analysis cycle are eased. The same amount of reaction auxiliary liquid as the amount of liquid to be suctioned by the suction nozzle 205 is supplied before the next suctioning of the reaction auxiliary liquid (e.g., at the same time or immediately after the liquid is suctioned by the suction nozzle 205). Thus, the amount of solution in the reaction auxiliary liquid container 304 is minimized and maintained unchanged. This prevents the spill and bubbling of the liquids in the containers during transfer. Consequently, the rotation and vertical movement of the container retaining member 211 are stabilized to improve analysis cycle efficiency and analysis performance.

A flow path connected to the reaction auxiliary liquid supply nozzle 303 is connected to the flow path 603, which communicates with a reaction auxiliary liquid supply source, through the reaction auxiliary liquid piping 403 in the hollow of the rotation shaft of the container retaining member transfer mechanism 210 and through the temperature control mechanism 602 disposed external to the container retaining member transfer mechanism 210, and is disposed so as not to obstruct the rotation and vertical movement of the container retaining member 211. The temperature control mechanism 602 exercises control to maintain the supplied liquid at a predetermined temperature. The reaction auxiliary liquid is maintained at a predetermined temperature by the temperature control mechanism 602 and by the temperature retention mechanism 401 in the hollow of the rotation shaft of the container retaining member transfer mechanism 210. After the suctioning of the reaction auxiliary liquid by the suction nozzle 205 is terminated, the magnet drive motor 206 rotationally drives the magnet arm 207 through 90 degrees to remove the magnetic particle capture magnet 208 from the detection container 202. A detector 209 disposed external to the detection container then detects the detection marker for the magnetic particle complex in the detection container 202 to determine the quantity of a measurement target.

Step 4

Figure 13:
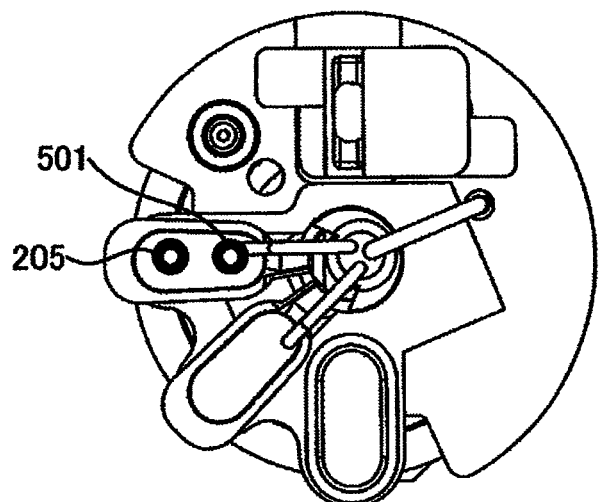
FIG. 13 is a plan view of the container retaining member transfer mechanism (cleaning liquid suction position).

After the detection of the detection marker is terminated, the container retaining member 211 moves downward to remove the suction nozzle 205 and the liquid level detection probe 501 from the reaction auxiliary liquid container 304. Next, the container retaining member 211 rotates to move the cleaning liquid container 305 to a location directly below the suction nozzle 205 as shown in FIG. 13. The container retaining member 211 then moves upward to insert the suction nozzle 205 and the liquid level detection probe 501 into the cleaning liquid. In this instance, the liquid level detection probe 501 detects the level of the cleaning liquid, and the amount of upward movement of the container retaining member 211 is controlled so that the depth of insertion of the suction nozzle 205 into the cleaning liquid is maintained at a predetermined value. Next, the suction nozzle 205 suctions the cleaning liquid in the same manner as described earlier and cleans the inside of the detection container 202 to eliminate the remaining magnetic particles and reaction auxiliary liquid. The cleaning liquid supply nozzle 302 is fixedly disposed on the container retaining member transfer mechanism 210 or on the container retaining member 211 so that the container retaining member 211 retains its relative positional relationship to the cleaning liquid container 305 even when the container retaining member 211 is rotating and vertically moving. Therefore, a steady, efficient liquid supply operation can be performed while limitations imposed by the operation of the container retaining member transfer mechanism 210 and by the analysis cycle are eased. The same amount of cleaning liquid as the amount of liquid to be suctioned by the suction nozzle 205 is supplied before the next suctioning of the cleaning liquid (e.g., at the same time or immediately after the liquid is suctioned by the suction nozzle 205). Thus, the amount of solution in the cleaning liquid container 305 is minimized and maintained unchanged. This prevents the spill and bubbling of the liquids in the containers during transfer. Consequently, the rotation and vertical movement of the container retaining member 211 are stabilized to improve analysis cycle efficiency and analysis performance.

A flow path connected to the cleaning liquid supply nozzle 302 is connected to the flow path 603, which communicates with a cleaning liquid supply source, through the hollow of the rotation shaft of the container retaining member transfer mechanism 210 and through the temperature control mechanism 602 disposed external to the container retaining member transfer mechanism 210, and is disposed so as not to obstruct the rotation and vertical movement of the container retaining member 211. The temperature control mechanism 602 exercises control to maintain the supplied liquid at a predetermined temperature. The cleaning liquid is maintained at a predetermined temperature by the temperature control mechanism 602 and by the temperature retention mechanism 401 in the hollow of the rotation shaft of the container retaining member transfer mechanism 210.

Step 5

Figure 14:
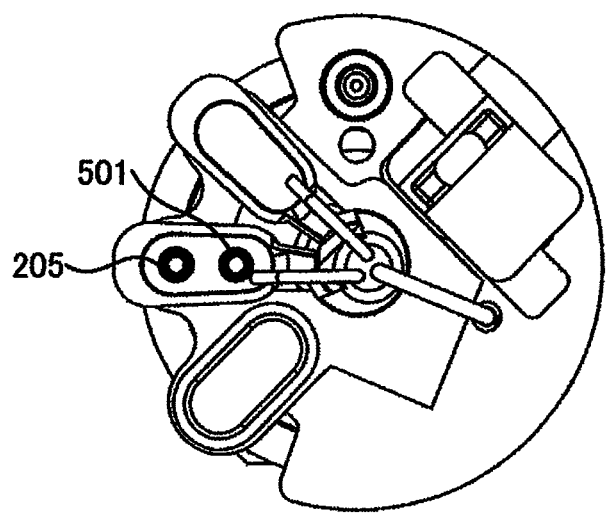
FIG. 14 is a plan view of the container retaining member transfer mechanism (reaction auxiliary liquid suction position).

After the suctioning of the cleaning liquid is terminated, the container retaining member 211 moves downward to remove the suction nozzle 205 and the liquid level detection probe 501 from the cleaning liquid container 305. Next, the container retaining member 211 rotates to move the reaction auxiliary liquid container 304 to a location directly below the suction nozzle 205 as shown in FIG. 14. The container retaining member 211 then moves upward to insert the suction nozzle 205 and the liquid level detection probe 501 into the reaction auxiliary liquid. In this instance, the liquid level detection probe 501 detects the level of the reaction auxiliary liquid, and the amount of upward movement of the container retaining member 211 is controlled so that the depth of insertion of the suction nozzle 205 into the reaction auxiliary liquid is maintained at a predetermined value. Positional arrangement is made so that the reaction vessel mounting place 301 can come close to the incubator disk 104 and to the reaction vessel transport mechanism 115 when the container retaining member 211 rotates and vertically moves. After the container retaining member 211 rotates and vertically moves, the reaction vessel 105, which is mounted on an incubator and retaining a reaction liquid into which a sample and a predetermined reagent were dispensed a predetermined period of reaction time ago, is transferred by the reaction vessel transport mechanism 115 to the reaction vessel mounting place 301 of the container retaining member 211. The suction nozzle 205 inserted into the reaction auxiliary liquid suctions the reaction auxiliary liquid in the same manner as for the suctioning of the reaction solution. The cleaning liquid remaining in the detection container 202 is then eliminated and substituted by the reaction auxiliary liquid to perform a preparation process for the next detection. The reaction auxiliary liquid supply nozzle 303 is fixedly disposed on the container retaining member 211 so that the container retaining member 211 retains its relative positional relationship to the reaction auxiliary liquid container 304 even when the container retaining member 211 is rotating and vertically moving. Therefore, a steady, efficient liquid supply operation can be performed while limitations imposed by the operation of the container retaining member transfer mechanism 210 and by the analysis cycle are eased. The same amount of reaction auxiliary liquid as the amount of liquid to be suctioned by the suction nozzle 205 is supplied before the next suctioning of the reaction auxiliary liquid (e.g., at the same time or immediately after the liquid is suctioned by the suction nozzle 205). Thus, the amount of solution in the reaction auxiliary liquid container 304 is minimized and maintained unchanged. This prevents the spill and bubbling of the liquids in the containers during transfer. Consequently, the rotation and vertical movement of the container retaining member 211 are stabilized to improve analysis cycle efficiency and analysis performance. A flow path connected to the reaction auxiliary liquid supply nozzle 303 is connected to the reaction auxiliary liquid supply source through the hollow of the rotation shaft of the container retaining member transfer mechanism 210 and through the temperature control mechanism 602 disposed external to the container retaining member transfer mechanism 210, and is disposed so as not to obstruct the rotation and vertical movement of the container retaining member 211. The temperature control mechanism 602 exercises control to maintain the supplied liquid at a predetermined temperature. The reaction auxiliary liquid is maintained at a predetermined temperature by the temperature control mechanism 602 and by the temperature retention mechanism 401 in the hollow of the rotation shaft of the container retaining member transfer mechanism 210.

Return to Step 1

After the suctioning of the reaction auxiliary liquid is terminated, the container retaining member 211 moves downward to remove the suction nozzle 205 and the liquid level detection probe 501 from the reaction auxiliary liquid container 304. Next, the container retaining member 211 rotates to move the reaction vessel 105 for the next analysis cycle to a location directly below the suction nozzle 205 as shown in FIG. 10. The container retaining member 211 then moves upward to insert the suction nozzle 205 into the reaction solution.

The automatic analyzer according to the present invention can efficiently perform a plurality of analyses by repeating the above-described analysis cycle in accordance with the flowchart of FIG. 15.

DESCRIPTION OF REFERENCE NUMERALS

100 . . . Automatic analyzer
101 . . . Rack
102 . . . Sample container
103 . . . Sample dispensing nozzle
104 . . . Incubator disk
105 . . . Reaction vessel
106 . . . Sample dispensing tip/reaction vessel transport mechanism
107 . . . Sample dispensing tip/reaction vessel retaining member
108 . . . Reaction vessel agitation mechanism
109 . . . Sample dispensing tip/reaction vessel disposal hole
110 . . . Sample dispensing tip mounting position
111 . . . Reagent compartment
112 . . . Reagent compartment cover
113 . . . Reagent compartment cover opening
114 . . . Reagent dispensing nozzle
115 . . . Reaction vessel transport mechanism
116 . . . Detection unit
117 . . . Rack transport line
118 . . . Reagent cassette
200 . . . Detection mechanism
201 . . . Flow path changeover valve
202 . . . Detection container
203 . . . Drain
204 . . . Liquid supply syringe
205 . . . Suction nozzle
206 . . . Magnet drive motor
207 . . . Magnet arm
208 . . . Magnetic particle capture magnet
209 . . . Detector
210 . . . Container retaining member transfer mechanism
211 . . . Container retaining member
212 . . . Flow path
301 . . . Reaction vessel mounting place
302 . . . Cleaning liquid supply nozzle
303 . . . Reaction auxiliary liquid supply nozzle
304 . . . Reaction auxiliary liquid container
305 . . . Cleaning liquid container
306 . . . Cleaning tank
307 . . . Special cleaning liquid container
401 . . . Temperature retention mechanism
402 . . . Hollow internal piping 403 . . . Reaction auxiliary liquid piping
404 . . . Cleaning liquid piping
405 . . . Drain piping
406 . . . Hollow portion
407 . . . Thermal insulator
408 . . . Cleaning tank drain
409 . . . Piping
501 . . . Liquid level detection probe
601 . . . Cover
602 . . . Reaction auxiliary liquid/cleaning liquid/suction nozzle cleaning liquid temperature control mechanism
603 . . . Reaction auxiliary liquid/cleaning liquid/suction nozzle cleaning liquid supply flow path
604 . . . Reaction auxiliary liquid/cleaning liquid/suction nozzle cleaning liquid flow path
605 . . . Circulating air temperature control mechanism
606 . . . Circulating air outlet
607 . . . Drain flow path

The invention claimed is:

1. An automatic analyzer comprising:
   a suction nozzle that suctions a solution used for the detection of a sample;
   a container that retains the solution used for the detection of the sample;
   a drive mechanism that drives a container retaining member to bring a container for the sample and the container for the solution in proximity to the suction nozzle to allow suction of the sample and solution by the suction nozzle, respectively; and
   a nozzle that supplies the solution to the container that retains the solution,
   wherein the nozzle moves in accordance with the movement of the container moved by the drive mechanism.

2. The automatic analyzer according to claim 1,
   wherein a piping connected to the nozzle passes through the interior of the drive mechanism.

3. The automatic analyzer according to claim 2,
   wherein the drive mechanism is driven rotationally and vertically to drive the container remaining member so that the container comes in proximity to the suction nozzle to allow suction of the solution in the container by the suction nozzle; and
   wherein the piping connected to the nozzle is positioned toward the center of rotation of the drive mechanism rather than the container.

4. The automatic analyzer according to claim 1, further comprising:
   a temperature retention mechanism that maintains the solution supplied from the nozzle at a predetermined temperature.

5. The automatic analyzer according to claim 1,
   wherein the piping connected to the nozzle passes through the interior of the drive mechanism; and
   wherein a liquid maintained at a predetermined temperature by the temperature retention mechanism flows through the interior of the drive mechanism.

6. The automatic analyzer according to claim 5, further comprising:
   a cleaning tank into which the liquid flows;
   wherein the liquid in the cleaning tank is used to clean the suction nozzle.

7. The automatic analyzer according to claim 6,
   wherein a thermal insulator is disposed between a flow path through which the liquid flowing out of the cleaning tank passes and a flow path through which the liquid flowing into the cleaning tank passes.

8. The automatic analyzer according to claim 1, wherein the nozzle supplies to the container the same amount of solution as the amount of solution suctioned by the suction nozzle.

9. The automatic analyzer according to claim 1,
   wherein the nozzle supplies the liquid at a timing earlier than the timing at which the suction nozzle performs the next suctioning operation.

10. An automatic analyzer of claim 1, further comprising:
    a cleaning liquid container holding a cleaning liquid,
    wherein the drive mechanism drives the container retaining member to bring the cleaning liquid container in proximity to the suction nozzle to allow suction of the cleaning liquid by the suction nozzle,
    wherein another nozzle supplies the cleaning liquid to the cleaning liquid container,
    wherein the nozzle and the another nozzle moves in accordance with the movement of the container or the cleaning liquid container moved by the drive mechanism.

* * * * *